US012758244B2

(12) United States Patent
Längle et al.

(10) Patent No.: US 12,758,244 B2
(45) Date of Patent: Oct. 13, 2026

(54) SHAFT FOR A MEDICAL INSTRUMENT, COMPRISING A PROFILED GUIDE, MEDICAL INSTRUMENT, ROBOT, AND METHOD FOR PRODUCING A SHAFT

(71) Applicant: KARL STORZ SE & CO. KG, Tuttlingen (DE)

(72) Inventors: Dominik Längle, Mülheim (DE); Janosz Schneider, Donaueschingen (DE); Sven Axel Grüner, Trossingen (DE); Jochen Stefan, Wald (DE)

(73) Assignee: KARL STORZ SE & Co. KG, Tuttlingen (DE)

( * ) Notice: Subject to any disclaimer, the term of this patent is extended or adjusted under 35 U.S.C. 154(b) by 127 days.

(21) Appl. No.: 18/291,506

(22) PCT Filed: Jul. 25, 2022

(86) PCT No.: PCT/EP2022/070838
§ 371 (c)(1),
(2) Date: Jan. 23, 2024

(87) PCT Pub. No.: WO2023/006687
PCT Pub. Date: Feb. 2, 2023

(65) Prior Publication Data

US 2025/0000535 A1 Jan. 2, 2025

(30) Foreign Application Priority Data

Jul. 28, 2021 (DE) ..................... 10 2021 119 518.7

(51) Int. Cl.
*A61B 17/29* (2006.01)
*A61B 17/00* (2006.01)
*A61B 34/30* (2016.01)

(52) U.S. Cl.
CPC .......... *A61B 17/2909* (2013.01); *A61B 34/30* (2016.02); *A61B 2017/00526* (2013.01); *A61B 2017/2902* (2013.01)

(58) Field of Classification Search
CPC ................ A61B 17/2909; A61B 34/30; A61B 2017/00526; A61B 2017/2902;
(Continued)

(56) References Cited

U.S. PATENT DOCUMENTS 5,603,697 A 2/1997 Grundy et al.
5,830,214 A * 11/1998 Flom .................. A61B 18/1482 604/35

(Continued)

FOREIGN PATENT DOCUMENTS

WO WO-2020080938 A2 * 4/2020 ........... A61B 1/0055

OTHER PUBLICATIONS

International Preliminary Report on Patentability, Application No. PCT/EP2022/070838, mailed Jan. 18, 2024.

(Continued)

*Primary Examiner* — Tan-Uyen T Ho
*Assistant Examiner* — Cherie M Poland
(74) *Attorney, Agent, or Firm* — Brooks Kushman P.C.

(57) ABSTRACT

An elongated shaft for a medical instrument includes an end section that is angled relative to a longitudinal central axis of the shaft by means of a joint mechanism, and a tool is arranged on the end section which can be angled. Multiple guiding elements are guided through the interior of the shaft in the longitudinal direction and connects a drive to the joint mechanism. The shaft has an outer tube or an inner tube and an elongated profiled guide between the outer tube for guiding the guiding elements. The profiled guide includes a first contact point for contacting the outer tube or the inner tube such that a guide channel or multiple guide channels
(Continued)

is/are formed in the longitudinal direction between the outer tube and the profiled guide or between the profiled guide and the inner tube for guiding a guiding element or multiple guiding elements.

16 Claims, 5 Drawing Sheets

(58) Field of Classification Search
CPC ... A61B 1/0011; A61B 1/0055; A61B 1/0057; A61B 1/31; A61B 34/00; A61B 18/14; A61B 17/00; A61B 17/29; A61B 17/00234; A61B 17/3421; A61B 90/50; A61B 2017/003; A61B 2017/00305; A61B 2017/00309; A61B 2017/00323; A61B 2017/00327; A61B 2017/2905; A61B 2017/2906; A61B 2017/291; A61B 2017/2927; A61B 2017/2937; A61B 2017/3447; A61B 2017/347; A61B 2017/00296; A61B 2017/00314; A61B 2017/00318; A61B 2017/00331; A61B 2017/00336; A61M 25/0138; A61M 25/0147; A61M 25/0133; A61M 25/0136; A61M 25/0141; A61M 25/0144
See application file for complete search history.

(56) References Cited

U.S. PATENT DOCUMENTS

| | | | | |
|---|---|---|---|---|
| 2011/0071542 | A1 | 3/2011 | Prisco et al. | |
| 2012/0182631 | A1* | 7/2012 | Le | A61B 1/00009 359/822 |
| 2021/0378648 | A1* | 12/2021 | Thissen | A61B 17/29 |

OTHER PUBLICATIONS

International Search Report, Application No. PCT/EP2022/070838, mailed Nov. 22, 2022. ISA/European Patent Office.

* cited by examiner

SHAFT FOR A MEDICAL INSTRUMENT, COMPRISING A PROFILED GUIDE, MEDICAL INSTRUMENT, ROBOT, AND METHOD FOR PRODUCING A SHAFT

CROSS-REFERENCE TO RELATED APPLICATIONS

This application is the U.S. national stage of PCT/EP2022/070838 filed on Jul. 25, 2022, which claims priority of German Patent Application No. 10 2021 119 518.7 filed on Jul. 28, 2021, the contents of which are incorporated herein.

TECHNICAL FIELD

The disclosure relates to a shaft for a medical instrument, the elongate shaft extending in a longitudinal direction from a proximal end to a distal end and having at its distal end an end portion, the end portion being able to be deflected relative to a longitudinal center axis of the shaft by means of a distal-side hinge mechanism and a tool being arrangeable at the end portion able to be deflected, and a plurality of steering elements for connecting a proximal-side drive to the distal-side hinge mechanism being guided through the interior of the shaft in the longitudinal direction, the shaft comprising an outer tube or an inner tube aligned in the longitudinal direction around a longitudinal center axis. Moreover, the disclosure relates to a medical instrument, a robot, and a method for producing a shaft.

BACKGROUND

By way of their elongate shaft and within the scope of both medical and nonmedical applications, instruments and/or endoscopes are introduced into animal or human body cavities or into technical apertures, for example a pipeline, for inspection and/or manipulation purposes. In this respect, frequent use is made of instruments able to be deflected at the distal end, and these can be in the form of manually guided and/or robotic instruments. To allow the shaft of the instrument to be deflected, it is conventional for four or more steering wires and/or steering cables to be arranged around and/or through pivot members of a distal-side hinge mechanism.

In the case of a shaft tube without guidance of the steering elements between the proximal end and the distal end of the shaft there is the risk of the shaft tube bending when wire tension is applied. Moreover, steering is impaired if the shaft tube is bent for other reasons. Moreover, the steering wires and/or current-conducting wires are not electrically insulated from one another.

For exact and homogenous control of the distal end able to be deflected of the shaft and/or robotic arm, the use of many thin steering elements is advantageous in order to enable a uniform movement and force distribution in all deflection directions. However, this places great demands on the assembly of the shaft since the latter, at the outset, has a very small diameter of a few millimeters on account of the introduction into a body cavity or technical aperture, since the many steering wires need to be threaded through the interior of the shaft over the entire length of the shaft and since said steering wires need to be attached in a tensioned state both on the distal side (remote from the user) and on the proximal side (near the user). In this context there is the risk of the steering wires becoming twisted and/or mixed up during the threading, and this may lead to an incorrect deflection of the distal end portion of the shaft. Moreover, steering wire wear may occur in the case of insufficiently tight guidance and/or tangling-up due to friction. Consequently, the performance of the instrument may be impaired, or the latter may even become damaged.

Although the practice of placing individual guiding elements with radial spacing within the shaft between the proximal end and the distal end of the shaft for the purpose of guiding steering wires is known, this however avoids the aforementioned problems only in part. Moreover, there is the risk of these guiding elements being displaced within the shaft, for example on account of the manipulation of a pull/push rod for opening and closing a tool at the distal tip of the instrument, and this in turn leading to the steering wires twisting.

U.S. Pat. No. 5,603,697 A has disclosed a medical catheter for insertion in a vessel in the body of a patient, wherein the catheter comprises a flexible tubular element with a plurality of lumina and a single steering wire is guided in said catheter in a steering wire support tube, wherein the tip of the catheter can be controlled by pulling the steering wire.

SUMMARY

It is an object of the disclosure to improve the prior art.

This object is achieved by a shaft for a medical instrument, the elongate shaft extending in a longitudinal direction from a proximal end to a distal end and having at its distal end an end portion, the end portion being able to be deflected relative to a longitudinal center axis of the shaft by means of a distal-side hinge mechanism and a tool being arrangeable at the end portion able to be deflected, and a plurality of steering elements for connecting a proximal-side drive to the distal-side hinge mechanism being guided through the interior of the shaft in the longitudinal direction, the shaft comprising an outer tube or an inner tube aligned in the longitudinal direction around a longitudinal center axis and the shaft comprising, between the outer tube and the longitudinal center axis or outside around the inner tube, an elongate contoured guide for guiding the steering elements, the contoured guide in the cross section across the longitudinal direction having a contour shape and the contour shape having at least a first contact point with the outer tube or with the inner tube, with the result that, between the outer tube and the contoured guide or between the contoured guide and the inner tube, one or more guide channels are formed in the longitudinal direction for guiding one or more steering elements.

As a result, the steering elements are guided from the proximal end to the distal end of the shaft, in each case individually or spaced apart from one another within the respective guide channel of the contoured guide, whereby the steering elements becoming twisted among themselves and hence a formation of an unwanted cord is prevented. Moreover, wear of the steering elements as a result of rubbing against one another is prevented on account of the targeted guidance in the respective guide channel. As a result of the targeted, individual guidance of a respective steering element or a plurality of spaced apart steering elements through a hollow guide channel of the contoured guide and the exclusion of twisting and/or rubbing of the steering elements with and against one another, incorrect deflection of the distal end portion of a medical instrument is prevented and the performance of the distal hinge mechanism is improved. Consequently, the performance of the medical instrument overall is optimized and damage thereof on account of suboptimal guidance of the steering elements within the shaft is precluded.

As a result of a steering element preferably being guided in each case through a guide channel formed between contoured guide, and hence the contour shape in cross section, and the outer tube and/or the inner tube during the assembly, an inadvertent mix-up and/or twisting of the steering elements is already prevented during the insertion of the steering elements into the shaft. Consequently, the assembly is simplified on account of the pre-sort of the steering elements by way of the individual guide channels of the contoured guide.

Moreover, a shaft with a wear-free individual guidance of steering elements through guide channels within and around the contoured guide is provided. This is advantageous in the case of steering cables in particular, as these are more susceptible to wear as a result of friction on account of their structured surface. Consequently, the contoured guide with its specific contour shape in cross section ensures optimal guidance of, and protection for, the steering elements, especially steering cables, in the shaft tube. In this case, it is advantageous that the targeted guidance of the individual steering elements in respective guide channels or guide channel regions matched thereto is implemented over the entire shaft length, in particular from the proximal end of the shaft to the distal end portion able to be deflected of the distal-side hinge mechanism.

In addition to simplified assembly and secure guidance of the steering elements, the contoured guide increases the stiffness of the shaft on account of one or more contact points on the inner surface of the outer tube and/or on the outer surface of the inner tube. As a result, the shaft according to the disclosure is suitable both for hand-guided instruments and for instruments guided by a surgical robot. Hence, the contoured guide, by way of its specific contour shape and the targeted arrangement of the contact points, reinforces the interior of the shaft and thus increases the latter's stiffness. In this case, the contour shape in the cross section of the contoured guide is shaped such that, in addition to the maximum stiffness possible, there is sufficient space for the targeted lead-through of steering elements, current-conducting wires, and/or manipulation elements.

A core idea of the disclosure is that of using a contoured guide with a specifically shaped contour shape in cross section to provide guide channels between the outer surface of the contour shape and the inner surface of the outer tube and/or the inner surface of the contour shape and the outer surface of the inner tube, for the purpose of guiding steering elements in the longitudinal direction of the contoured guide and hence of the shaft, whereby these are guided separately from one another and hence precisely not freely through a shaft tube from the proximal end to the distal end. As a result, the steering elements can be un-mistakably threaded, without crossing and on an individual basis, for the purposes of assembling the shaft. It is particularly advantageous that the contour shape of the guide channel can precisely be chosen freely and hence can be freely matched to the number and the respective diameter of the steering elements, power cables to be guided through, and manipulation elements.

In principle, it should be stressed that on account of the tight spatial conditions in the narrow shaft with a diameter of only a few millimeters the prevalent opinion to date was precisely that of providing clear space between the steering elements and the further components in the interior of the shaft. By contrast, according to the disclosure, the interior of the shaft is now partially filled in a targeted manner by the contoured guide with the specific contour shape in cross section.

The following concepts shall be explained:

In particular, a "shaft" is an elongate and hollow tube for at least partial insertion into a body cavity and/or a technical aperture. In particular, a shaft can be a flexible and/or stiff shaft. In the case of a stiff shaft, the distal end portion in particular is designed to be able to be deflected. The shaft has in particular a diameter ranging from 2 mm to 10 mm. In its interior, the shaft may in particular comprise further components, for example an optical waveguide for illuminating an object field, one or more work channels for supplying an irrigation fluid or tool, for instance a biopsy needle or an electrode. Especially in the case of a rigid shaft, a central manipulation element for manipulating a tool, for example a jaw part, at the distal end portion able to be deflected can be arranged in the interior of the shaft from its proximal end to its distal end. At its proximal end, the shaft is mechanically and/or electrically connectable to a handling unit of a medical or industrial instrument in particular.

The "longitudinal direction" of the shaft is the direction of longest extent of the shaft. Accordingly, the "longitudinal center axis" of the shaft is the axis corresponding to the direction of its longest extent.

A "medical instrument" is in particular any mechanical or mechanical/electrical unit of action which is suitable for the diagnosis and/or treatment of humans or animals. The medical instrument is used in particular for inspection of a human or animal body cavity and/or for manipulation of human or animal tissue. In particular, the medical instrument comprises a grip or handle, a shaft, and a tool, and/or an optical system for observing a field of view. The medical instrument can have in particular a gripping tool, a cutting tool, a needle holder, a clip applicator, and/or another kind of tool. For example, a medical instrument is an endoscope, with a long shaft and an end portion able to be deflected. The medical instrument can be a hand-held and/or hand-guided instrument. The medical instrument can also be arranged on a robotic arm of a surgical robot as an end effector and consequently be a robot-assisted instrument.

In particular, a "hinge mechanism" comprises a "distal-side hinge mechanism" and a "proximal-side hinge mechanism". In particular, the "proximal-side hinge mechanism" comprises a spatially adjustable plate, associated spindles, and the proximal-side steering element portions. On the distal side of the proximal-side hinge mechanism and in the direction toward the distal tip, the steering elements in particular are brought together, for example by way of a guide ring or a fanning plate, to a shorter distance of the steering elements from the longitudinal axis of the shaft, with the result that these steering elements enter the proximal end of the shaft substantially parallel to one another and are guided substantially parallel to one another to the distal end portion within the shaft. On the distal side of the proximal-side hinge mechanism, the associated spindle of the spatially adjustable plate, in particular, is connected to a main spindle in the distal direction, with the rotation of the shaft being realizable by way of said main spindle. The hinge mechanism can be arranged in particular in the transition region between handle and/or holding part of the medical instrument and the shaft, or in the handle and/or holding part. In particular, the "distal-slide hinge mechanism" comprises the distal-side steering element portions and the pivot members and/or member bodies, by means of which the distal end portion can be deflected.

A "proximal drive" is in particular a drive unit for bringing about a movement of the steering elements. In particular, the proximal drive can bring about an action on or a pivoting of a spatially adjustable plate (wobble plate). Consequently, the drive movement of the proximal drive in particular is transferred into a pivot movement of the spatially adjustable plate and, by way of the steering elements fastened to the spatially adjustable plate on the proximal side, the drive movement is transferred to a corresponding relative movement of the distal-side pivot members and/or member bodies of the distal-side hinge mechanism for pivoting the end portion of the instrument. The proximal drive can be a manual drive on account of, for example, a rotary movement of a manipulation element on the handling unit of the instrument or a motorized drive. In the case of a motorized drive, the latter comprises one or more motors and/or a gear, for example driven gear wheels. In particular, the proximal drive is arranged in the handling part and/or in the holding part of the instrument.

In particular, a "steering element" is a thin and long, shaped pliable element. In particular, the elongate steering element comprises metal, metal alloy, and/or plastic. A steering element can be a steering wire and/or a steering cable. In particular, a "steering wire" is a thin and long, shaped pliable metal. In particular, a steering wire contains a nickel-titanium alloy, and hence Nitinol, stainless steel, for example a stainless austenitic chromium-nickel-molybdenum steel (1.4401), and/or tungsten. In particular, the steering wire has a smooth surface. A steering cable is an elongate, high tensile strength element consisting of twisted or braided, natural or artificial fibers or wires. In accordance with the twisting together or braiding, a steering cable may have a structured surface in particular. However, a steering cable may also be cladded with plastic in order to have a smooth surface. In principle, a steering element may have any cross-sectional shape, for example a circular, oval and/or bent cross section, or a flat edge, square, or contoured wire cross section. The steering element preferably has a round cross section. Conventionally, >3 or 4, preferably 10 or any number of steering elements are used in a hinge mechanism in the interior of the shaft. In addition to the proximal-side attachment of the steering element ends to the spatially adjustable plate, the opposite distal steering element ends are each affixed on the inside to the distal end portion able to be deflected. A steering element can also be a current-conducting wire or a light guide.

In principle, it should be observed that, instead of a steering element or in addition to a steering element, a current-conducting wire, a manipulation element, an electrode, or similar may also be guided through a guide channel formed by the contoured guide.

A "current-conducting wire" is an electrical conductor in particular. In particular, the current-conducting wire serves to transport electrical power and/or transmit signals. A current-conducting wire can also be a thin elongate electrode.

In the region of the distal end portion able to be deflected, the steering elements are arranged around pivot members and/or member bodies in external radially circumferential fashion and/or arranged therethrough, said pivot members and/or member bodies realizing delicate deflecting of the distal end portion. By way of a movement of the spatially adjustable plate brought about by means of a proximal drive, and by way of the steering elements connected to the plate and tensioned along the longitudinal direction of the shaft up to the distal steering element ends affixed in the distal end portion, a corresponding relative movement is transferred to the distal-side pivot members, and hence deflection of the distal end portion is brought about. To this end, a multiplicity of thin steering elements in particular is used for a fine-motor control of the distal end portion of the medical instrument, in order to obtain a more uniform force distribution and hence relative movements in all possible deflection directions.

In particular, a "manipulation element" (also referred to as "manipulation train") is an element whose movement manipulates a tool. In particular, a manipulation element can be a pull/push rod or cable and/or a transmission element for a rotary movement. For example, the manipulation element is used to open and close a two-part jaw part of a tool. In particular, the manipulation element is guided centrally in the interior of the shaft, along the longitudinal center axis from the proximal end to the distal end of the shaft.

In particular, an "outer tube" or an "inner tube" is an elongate hollow body, whose length is substantially greater than its diameter. In particular, the outer tube or the inner tube has a circular cross section. Preferably, the outer tube and/or the inner tube is arranged coaxially with respect to the longitudinal center axis of the shaft. In particular, the outer tube forms the outer surface of the shaft and/or the external shaft. However, in place of the outer tube, a tubing, in particular a heat-shrink tubing, may also be arranged around the contoured guide. Likewise, the shaft may not have an inner tube and may form a clear space, an inner cavity of the shaft, surrounded by the inner diameter of the contour shape of the contoured guide. While the outer tube and/or the inner tube are/is preferably formed from coaxial tubes, the contoured guide preferably precisely does not have a circular contour.

In particular, a "contoured guide" is a hollow elongate component with a contour shape in cross section, wherein the contour shape forms one or more guide channels on the inner surface of the contoured guide and/or on the outer surface of the contoured guide. The contour shape preferably is the same over the entire length of the contoured guide. In particular, the contour shape forms guide channels in the longitudinal direction which are separated from one another by way of one or more contact points with the outer tube and/or inner tube. The contour shape of the contoured guide is preferably not arranged in a circular fashion with respect to the longitudinal center axis of the shaft but has various curved sections. However, the contoured guide may also be formed by one or more standard tubes. To this end, a plurality of standard tubes adjacent to one another in circular fashion may form the contoured guide, wherein at least one standard tube has a contact point with the inner tube and/or outer tube. Likewise, one or more standard tubes may have only one contact point, in each case with the outer tube or with the inner tube. Should the standard tube be connected to the outer tube only on the inside by way of a contact point, the standard tube firstly forms a guide channel in its interior and secondly forms a further guide channel on the outside between the outer surface of the standard tube, in the clear space to the inside inner tube. In principle, the contour shape of the contoured guide in cross section may have any outer shape, for example a square, triangular, polygonal, circular, bent, oval and/or star-shaped outer shape. In particular, the outer shape of the contour shape may also change from one contact point to the adjacent subsequent contact point. For example, the contoured tube can be bent outwardly from the first contact point of the contoured guide on the inner tube to the second contact point on the outer tube, and can have a straight line embodiment from the second contact point on the outer tube to the third contact point on the inner tube.

The contoured guide and hence the contour shape in cross section is arranged in particular around the inner tube on the outside or in a manner surrounded by the outer tube, or between the inner and outer tube. The contoured guide, the outer tube, and/or the inner tube may have the same length and/or different lengths. In particular, the contoured guide may have a slightly shorter length in comparison with the inner tube and/or the outer tube and thereby have an offset embodiment, with the result that a tube socket of the distal-side hinge mechanism is connectable to the contoured guide.

In particular, a "contact point" is a point at which contact is established between the contour shape of the contoured guide and the inner surface of the outer tube or between the contoured guide and the outer surface of the inner tube. In cross section, the contact point can be a contact spot or a more elongate contact area. Preferably, each contact point is formed over the entire length of the contoured guide in the longitudinal direction. However, a plurality of interrupted contact points may also be formed in the longitudinal direction of the contoured guide. Each contact point can be an integral bond and/or frictional connection between the contoured guide and the outer tube or inner tube. The otherwise usually contiguous ring-shaped clear space within the shaft is subdivided into a plurality of guide channels by way of the positioning and number of the contact points on the outer tube and/or inner tube, and hence by way of the profile of the contour shape.

In particular, a "guide channel" (also referred to as "lumen") is a contiguous cavity in the longitudinal direction of the shaft, which is formed on account of the contour shape of the contoured guide between the outer surface of the contoured guide and the inner surface of the outer tube and/or between the inner surface of the contoured guide and the outer surface of the inner tube. Consequently, outside guide channels are provided between the inner side of the outer tube and the outer side of the contoured guide and/or inside guide channels are provided between the inner side of the contoured guide and the outer side of the inner tube, by way of the positions and number of the contact points and the profile of the contour shape. In particular, the guide channel is designed parallel to the longitudinal center axis of the shaft. In principle, each guide channel can have any cross-sectional shape, for example a circular, bent, square, rectangular, or triangular shape, or similar. The cross-sectional shape of the respective guide channel preferably has a nonsymmetric embodiment. The cross-sectional shape of the guide channel may also vary over the length of the guide channel. In particular, the guide channel has a larger cross section than the outer diameter of the guided steering element, current-conducting wire, and/or manipulation element, with the result that the guided object can in each case move freely within the guide channel.

In principle, it should be stressed that there is no need for a steering element to be guided through each guide channel formed by the contoured guide; instead, there may also be one or more guide channels which do not contain a steering element. Likewise, two or more steering elements may also be guided through a single guide channel. To this end, the contoured guide may be shaped such that a guide channel has two or more specific guiding regions in cross section, through which adjacent steering elements are guided, largely spaced apart from one another in space, through the same guide channel. To form the guide regions, the guide channel may in each case have an appropriately bent cross-sectional shape portion of the contour shape.

In a further embodiment of the shaft, the contour shape has a second contact point, a third contact point, a fourth contact point, a fifth contact point, and/or further contact points.

As a result, a plurality of guide channels may be provided, in a manner corresponding to the number of contact points, and the static and dynamic stiffness of the shaft can be set in a targeted manner. By way of the connection, via the contact points, of the contoured guide to the outer tube and/or inner tube, these are braced against one another in each case. In addition to an increase in the stiffness, this can also effectively dissipate forces that act during the use of the shaft, and an optimal vibration and/or damping behavior can be obtained.

A multiplicity of different shapes of the contour shape can be realized by way of the chosen number and respective position of the contact points. By increasing the number of contact points, and hence number of guide channels, it is moreover possible to adapt the cross-sectional shape of each guide channel, and hence the shape of the contour shape, and consequently, as the numbers increase, it is possible to have a denser arrangement of guide channels.

It is particularly advantageous that, depending on the number of guide channels, geometric basic shapes and respectively required diameters of the outside guide channels, inside guide channels, outer tube and/or inner tube, and overall diameter of the shaft, it is possible to set the manufacturability of the shaft and its product properties in a targeted manner by way of the choice of the respective wall thicknesses of the outer tube, contoured guide, and/or inner tube, and the exact shape of the contour shape.

Preferably, the outer tube and/or the inner tube in cross section have a wall thickness ranging from 0.25 to 0.75 mm, in particular from 0.35 to 0.65 mm, and preferably from 0.45 to 0.55 mm. By contrast, the contour shape preferably has a thinner wall thickness than the outer tube and/or the inner tube, for example ranging from 0.20 to 0.40 mm, and preferably from 0.25 to 0.35 mm.

A second, third, fourth, fifth, and/or further contact point is an above-defined contact point in terms of embodiment and function.

To specify the cross-sectional shape of the respective guide channel adjacent to the contour shape, the contour shape has a tapered, conical, bent or rib-type form in cross section at the respective contact point.

In particular, "rib" is understood to mean that the contour shape is bent back through 180° at the contact point such that two adjacent inner sides of the contour shape are arranged between the outer diameter of the contour shape and the outer diameter of the inner tube or between the inner diameter of the outer tube and the inner diameter of the contour shape and together form a rib.

In a further embodiment of the shaft, the contour shape is radially symmetrical, polysymmetrical, and/or asymmetrical in cross section.

In particular, "radially symmetrical" is understood to mean that the contour shape in cross section is invariant vis-à-vis all rotations.

In particular, "polysymmetrical" is understood to mean that the contour shape in cross section has a plurality of planes of symmetry. Thus, the contour shape may also have a three-fold or multifold, polysymmetrical form of symmetry with a plurality of planes of symmetry running like rays through the longitudinal axis, in which identical parts are arranged in a circular, three-dimensional fashion about a central axis (axis of rotation), wherein the contour shape is defined by the outer form of symmetry.

In particular, "asymmetrical" is understood to mean that the contour shape in cross section, with its specific cross-sectional shape profiles between the contact points, cannot be made congruent, not by rotation and not by reflection or translation either.

To form a regular profile of the contour shape between the respective contact points, the contour shape has a star contour or a flower contour in cross section.

In particular, a "star contour" is understood to mean a geometric shape of the contour shape in cross section, in which the contact points of the contour shape are formed as a regular polygon with respect to one another, such that in particular the distances between the contact points are of the same length in each case. In this case, the limbs of the contour shape formed as a star contour which run toward the respective contact point, and hence the polygon and/or star tips, need not necessarily have a pointed or angular embodiment at the contact point but may also be arced at the contact point. In particular, the star contour can be regular and consequently be mirror symmetrical and/or rotationally symmetrical. However, the star contour may also have an irregular shape in cross section. Likewise, the polygon and/or star tips may have a regular and/or irregular arrangement in cross section.

In the case of a "flower contour", the contour shape in cross section has the outer shape of a flower in particular. Accordingly, the inner guide channels aligned with respect to the longitudinal center axis of the shaft and/or with respect to the inner tube are formed in the shape of a petal. In particular, as a flower contour, the contour shape is shaped such that the latter forms three or more petals. The flower contour itself may have a regular or an irregular shape in cross section. Likewise, the petals of the flower contour may have a regular and/or irregular arrangement in cross section.

In order to be able to form the shaft without an outer tube or inner tube, in the cross section with the contact points the contour shape forms an approximately closed shape at its outer diameter or at its inner diameter.

As a result of all contact points being formed on the inner side of the outer tube and having a design that is bent with very tight radii such that the contour shape has outwardly protruding ribs, the inside walls of the contour shape are very extensive and adjoin one another in the inner region of the rib, with the result that an approximately closed shape is formed. As a consequence of the contour shape consequently almost surrounding a cavity on the inside, it is possible to dispense with an inner tube. Likewise, the ribs can protrude inwardly with contact points of little extent arranged on the inner tube, with the result that the contour shape is embodied as a largely closed shape along the inner diameter of the outer tube. Consequently, it is likewise possible here to dispense with an outer tube and for example pull a heat-shrink tubing over the outer diameter of the contour shape, and hence of the contoured guide, in place of an outer tube.

An "approximately closed shape" is understood to mean that the respective side walls of the contour shape are adjacent to one another on account of very tight bending radii and, on the opposite side, the walls of the contour shape approximately form a closed outer shape or inner shape on account of the large radial extent at the outer diameter or inner diameter of the contour shape.

In order to electrically insulate the shaft and/or prevent an ingress of liquid into the shaft, an insulation tubing is arranged around the contoured guide.

Consequently, it is also possible to guide electrical wires or electrodes through a guide channel of the shaft.

In particular, an "insulation tubing" is a tubing made of plastic. For example, a heat-shrink tubing which, as thermoplastic tubing, contracts significantly in the radial direction under the action of heat can be used as insulation tubing. The heat-shrink tubing can be applied directly to the outer diameter of the contoured guide. Hence, the insulation and/or heat-shrink tubing can directly replace the outer tube, with the result that the outer tube can be dispensed with. However, a heat-shrink tubing can likewise also be additionally applied to an outer tube, for example if the outer tube contains metal and is consequently electrically conductive.

In a further embodiment, the shaft comprises the outer tube and the inner tube.

As a result, the contoured guide can be arranged between outer tube and inner tube and provide a further reinforcement of the shaft and further guide channels arranged inside toward the inner tube and further guide channels arranged outside toward the outer tube.

In order to realize diverse arrangement possibilities of the outer tube, contoured guide, and/or inner tube with respect to one another, the outer tube, the contoured guide, and/or the inner tube is or are arranged coaxially with or off-center in relation to the longitudinal center axis of the shaft.

Preferably, the outer tube and the inner tube are each arranged coaxially with the longitudinal center axis of the shaft and have a circular embodiment in cross section, while the contoured guide has a non-round contour and/or is arranged off-center. However, the inner tube may also be arranged off-center at or in the vicinity of the inner side of the outer tube and the clear space in the interior of the outer tube present as a result can be formed by the contoured guide with its contour shape and corresponding guide channels. As a result of the contour shape being off-center and hence located away from the circle center of the longitudinal center axis of the shaft, a free design of the shape profile of the contour shape is rendered possible.

In cross section the contact points in a further embodiment are arranged alternately on the outer tube and the inner tube along the contour shape.

As a result of the contour shape alternately connecting the contact points on the outer tube and on the inner tube, a regular structure and bracing is obtained, whereby, similar to the design of corrugated cardboard, the bracing results in a very stable interior of the shaft, and hence a high strength and stiffness of the entire shaft. As a result, forces acting on the shaft from the outside can be optimally absorbed to the inside, dissipated, and distributed, whereby the shaft has a good vibration and damping property.

To increase the stiffness at the outer tube in a targeted manner, the contact point or the contact points on the outer tube each have a greater contact area than the contact point or the contact points on the inner tube, with the result that outer tube is stiffened at the respective contact points.

Likewise, the stiffness and strength at the inner tube can be increased by virtue of the contact point or the contact points on the inner tube each having a greater contact area than the contact point or the contact points on the outer tube, with the result that the inner tube is stiffened at the respective contact point.

To open and/or close a tool at the distal end portion able to be deflected of a medical instrument, an elongate manipulation element for manipulating the tool is guided in the inner tube and/or in a hollow channel formed by the contoured guide.

In principle, it should be stressed that the elongate manipulation element, for example a pull/push rod, can be guided in a middle central channel in the inner tube, in a middle hollow channel surrounded by the inner diameter of the approximately closed shape of the contour shape, or else in a guide channel. In this case, it is naturally also possible to guide two elongate manipulation elements for manipulating different tools through the central channel, a hollow channel formed by the contoured guide, and/or a guide channel or plurality of guide channels. One of these embodiments with the protected guide of the manipulation element in a separate channel prevents the back and forth movement of the manipulation element when opening and closing the tool from influencing the steering elements likewise arranged in protected fashion in the guide channels. When guiding the elongate manipulation element in a cavity formed by the contoured guide, it is consequently possible to dispense with an inner tube.

In a further embodiment of the shaft, the outer tube, the inner tube, and/or the contoured guide contain a metal, a metal alloy, plastic, and/or a fiber-reinforced material.

Firstly, the outer tube, the inner tube, and/or the contoured guide can be fabricated from the same or similar material and can be connected, both in simplified fashion. Secondly, this advantageously also allows the targeted selection of different materials for the outer tube, the inner tube, and/or the contoured guide. For example, the contoured guide can be drawn from steel as a star contour, while the outer tube made of plastic is pushed onto the fabricated contoured guide and hence frictionally connected to the latter. In place of the increased stiffness on account of a metal-containing contoured guide in the interior of the shaft, the contoured guide may however also contain plastic in a targeted manner, for example in order to minimize friction between steering wires and the inner walls of the guide channels made of plastic, and hence minimize wear of the steering wires, in the case of steering wires fabricated from metal. In addition to insulation, the lower weight and the higher damping behavior in the case of vibrations in particular are also advantages of plastic.

As a result of the outer tube being in the form of a plastic tube, there is no need for an additional heat-shrink tube for insulation purposes in the case of electrical applications of the shaft. To obtain an appropriate stiffness of the plastic tube in the case of the constant overall diameter, the outer tube designed thus may have a greater wall thickness, whereby the lower stability of plastic vis-à-vis a steel tube can be compensated for.

By combining plastic and for example steel when designing the outer tube, inner tube, and/or contoured guide, which have different elasticities, it is possible here to dynamically exploit advantageous synergies in the individual properties of the constituent parts of the shaft. Consequently, the respectively envisaged shaft property can be set in a targeted manner by variation and targeted material selection for the individual constituent parts of the shaft.

In particular, a “fiber-reinforced material” can be a composite material which, in particular, is reinforced with ceramic, organic, polymer, and/or metallic particles and/or fibers. For example, a fiber-reinforced material can be a glass fiber-reinforced, carbon fiber-reinforced, and/or ceramic fiber-reinforced material.

To implement an optimal press fit within the scope of joining when fabricating the shaft, the fibers of the fiber-reinforced material are aligned in radially circumferential fashion around a longitudinal center axis of the outer tube, inner tube, and/or contoured guide.

As a result of the circumferential fibers of the fiber-reinforced material in the outer tube, inner tube, and/or contoured guide, the forces on account of the press fit during the joining and the subsequent press fit are optimally absorbed and distributed.

In a further aspect of the disclosure, the object is achieved by a medical instrument having an elongate shaft and a handling unit connected to the shaft, with the handling unit rendering manipulatable a proximal drive of a distal-side hinge mechanism and/or an elongate manipulation element for manipulating a tool at an end portion able to be deflected at the distal end of the shaft, wherein the shaft is an above-described shaft, with the result that one or more steering elements are guided through one or more guide channels in the contoured guide.

This provides a medical instrument in which the shaft according to the disclosure is electrically and/or mechanically connectable to the handling unit of the medical instrument and, on account of the individual and optimal guidance of the steering elements through the guide channels of the contoured guide within the shaft, a very accurate, very delicate and long-term reproducible deflecting of the end portion able to be deflected of the shaft of the instrument is rendered possible. Naturally, for the purpose of forming the medical instrument, the shaft may also be connected securely and hence non-releasably to the handling unit.

In an additional aspect of the disclosure, the object is achieved by a robot having at least one robotic arm for holding and/or positioning a medical instrument and/or having an actuator for controlling a distal-side hinge mechanism of the medical instrument, wherein the medical instrument is an above-described medical instrument, with the result that the medical instrument is positionable by means of the at least one robotic arm and/or the distal-side hinge mechanism is manipulatable by the action of the actuator of the robot on the proximal drive of the medical instrument.

As a result, the individual guidance of the steering elements within the guide channels by means of the contoured guide can ensure an optimally spaced apart movement of the steering elements and/or current-conducting wires, both in a hand-guided medical instrument and in a robotically guided instrument. Moreover, the material selection for the outer tube, inner tube, and/or contoured guide and the number of contact points of the contoured guide can be used to set a required flexural rigidity of the contoured guide and/or shaft for a robot-assisted instrument in a targeted manner.

In this case, the robot ensures, firstly, a secure hold of the medical instrument at the end of the at least one robotic arm and also a positionally accurate alignment of the medical instrument. Secondly, the hinge mechanism and the deflection of the distal end portion of the medical instrument as an end effector can be guided very accurately by way of an input device on the robot, for example by means of a joystick of a control console and/or input grips of the robot fastened to the hand. In principle, the proximal drive of the medical instrument may also be arranged in the distal end of the robotic arm and a coupling point and/or interface between the distal end of the robotic arm and the holding unit of the medical instrument can be designed accordingly.

In particular, a “robot” is a medical and/or surgical robot. In particular, a robot is an operation robot. The robot is usually a telemanipulator which on the one side uses the activators of the surgeon to control the medical instrument as end effector at the end of the robotic arm on the other side. The robot preferably comprises a plurality of robotic arms, wherein a camera, for example a three-dimensional camera, is arranged on one of the robotic arms in particular and one or more interchangeable medical instruments are arranged on a further robotic arm or on the other robotic arms. In particular, each robotic arm is designed to be moveable with respect to 3 to 8 axes. In place of a robot with a plurality of arms, it is naturally also possible to make use of a plurality of robots, each with one or else only two arms, with said robots being controlled together.

As a result of a coupling point and/or interface between the end of the robotic arm holding the medical instrument and the medical instrument, it is possible to actuate the proximal drive of the medical instrument by means of the actuator of the robotic arm. In this case, any drive-type component or assembly which converts an electrical signal into a mechanical movement can be used as an actuator.

In a further aspect of the disclosure, the object is achieved by a method for producing a shaft for a medical instrument having an outer tube and/or an inner tube, comprising the following steps:

- fabricating, in particular drawing, a contoured guide with a contour shape in the cross section to the longitudinal direction of the contoured guide with the formation of at least one guide channel in the longitudinal direction for the purpose of guiding one or more steering elements, and/or
- joining the contoured guide to the inner tube, and/or
- joining the outer tube to the contoured guide, with the respective joining being implemented in frictionally connected and/or integrally bonded fashion,
- and inserting or leading the steering element or steering elements into or through the at least one guide channel.

Hence, this provides a method for producing a shaft which, on account of the contoured guide and the guide channels formed thereby, enables a simplified assembly process for the steering elements. The contour shape of the contoured guide pre-sorts the steering elements already during the assembly, with the result that a mix-up of the steering elements is no longer possible.

It is particularly advantageous for the inner diameter of the outer tube to be slightly undersized vis-à-vis the outer diameter of the contoured guide and/or for the inner diameter of the contoured guide to be slightly undersized vis-à-vis the outer diameter of the inner tube such that a press fit arises during joining, and hence the outer tube and the contoured guide and/or the contoured guide and the inner tube are frictionally connected at the contact points. In addition to the frictional connection, there can, alternatively or cumulatively, also be integral bonding at the contact points between the outer tube and the contoured guide and/or between the contoured guide and the inner tube. For example, the integral bond at the contact points can be realized by means of an adhesive and/or solder at the contact points. In this case, it is advantageous that the capillary effect can be exploited and tight angular regions between the contour shape of the contoured guide and the outer tube and/or inner tube can be filled with adhesive or solder, with the result that tight regions, which are otherwise critical in respect of cleaning, can be avoided.

Further embodiments, and some of the advantages connected to these and further embodiments, are rendered clear and better understandable by the following detailed description which makes reference to the attached figures. Objects or parts thereof which are substantially the same or similar may be provided with the same reference signs. The figures are merely a schematic illustration of an embodiment of the disclosure. An exemplary embodiment of the disclosure is depicted in the drawings. The drawings, the description, and the claims contain numerous features in combination. A person skilled in the art will advantageously also consider the features on an individual basis and combine them to form further advantageous combinations.

Figure 1:
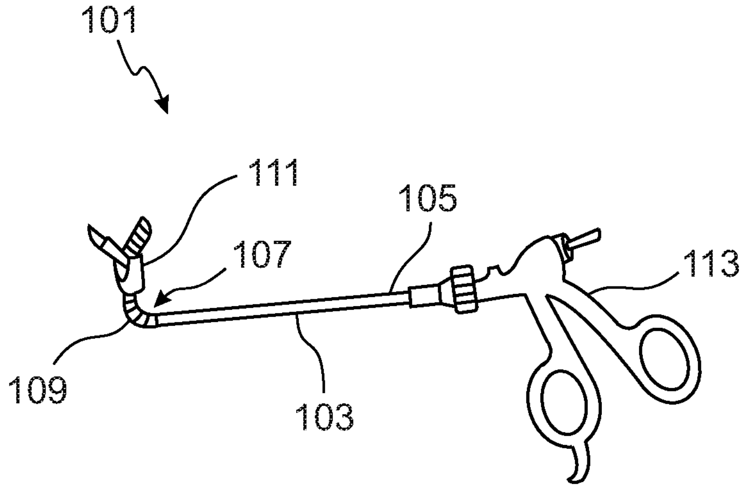
FIG. 1 shows a schematic three-dimensional illustration of a medical instrument with a jaw part tool.

A medical instrument 101 comprises a handle 113 enabling user control and an elongate shaft 103 which at its proximal end 105 adjoins the distal side of the handle 113. An end portion 109 able to be deflected and having a jaw part tool 111 at the end is arranged at an opposite distal end 107 of the shaft 103 (in FIG. 1, the jaw part tool 111 is depicted excessively large and not true to scale). To deflect the end portion 109 able to be deflected, a proximal-side hinge mechanism and a distal-side hinge mechanism are arranged in the interior of the shaft 103, wherein a deflection of the end portion 109 able to be deflected and an opening and closing of the jaw part tool 111 is able to be effected by means of the handle 113.

The elongate shaft 103 has a longitudinal center axis 115. Arranged in each case coaxially around the longitudinal center axis 115, there is an inner tube 125 on the inside and an outer tube 127 on the outside. To the outside, the outer tube 127 is surrounded by a heat-shrink tubing 157 for isolation purposes. In the interior cavity of the inner tube 125, a pull/push rod 119 is movably guided in a central channel 139 so as to manipulate the jaw part tool 111. A contoured guide 121 designed as a star contour 123 in cross section is arranged between the inner side of the outer tube 127 and the outer side of the inner tube 125. The star contour 123 alternately has outer contact points 131 to the inner side of the outer tube 127 and inner contact points 133 to the outer side of the inner tube 125. As a result, an outer guide channel 135 situated so as to be aligned to the outer tube 127 and an inner guide channel 137 aligned to the inner tube 125 alternate one another, respectively in succession, along the cross section (see FIGS. 3 and 6). Hence the shaft 103 has a five outer guide channels 135 and five inner guide channels 137, in each of which a steering wire 117 is guided. In the assembled state, the steering wires 117 are tensioned between the proximal end 105 of the shaft 103 and the end portion 109 able to be deflected.

Figure 2:
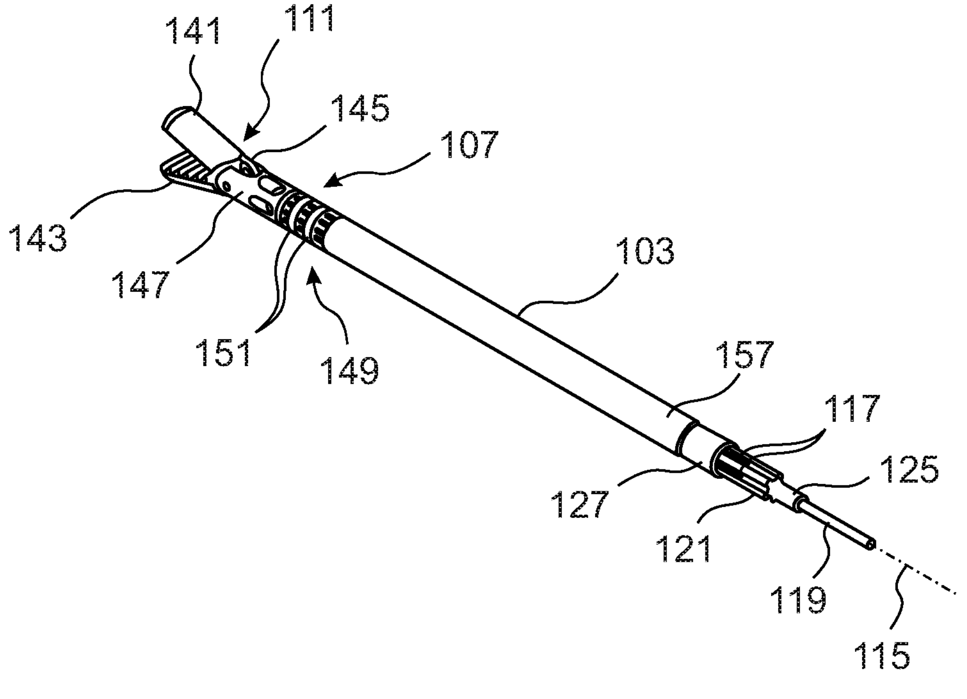
FIG. 2 shows a schematic three-dimensional illustration of the shaft with the jaw part tool and with a contoured guide inside.
Figure 4:
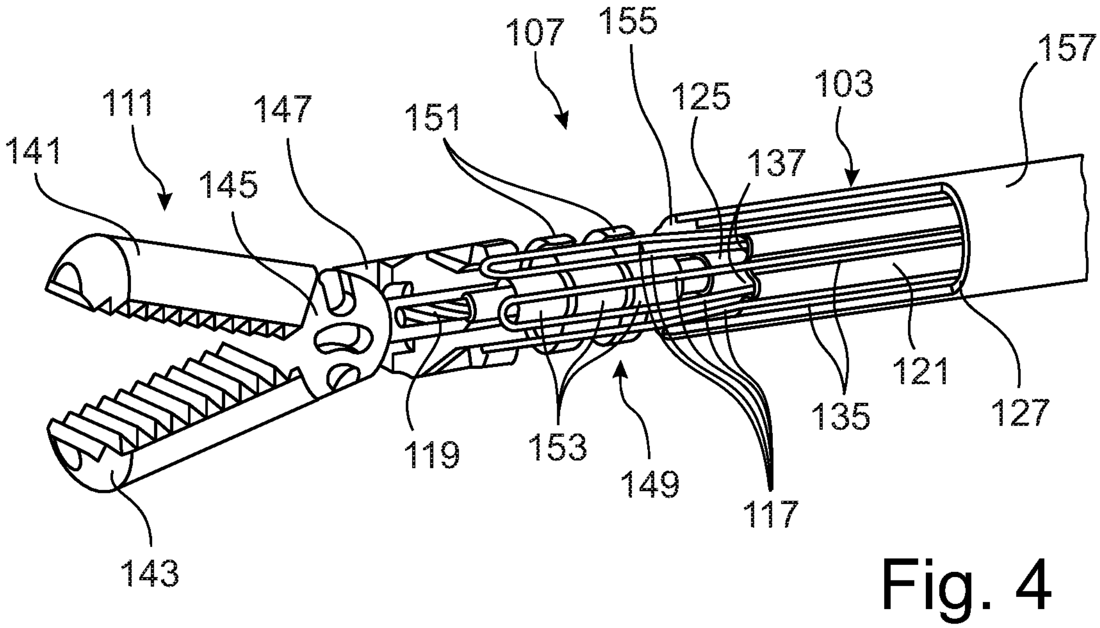
FIG. 4 shows a schematic three-dimensional illustration of a detail of the shaft with a distal-side deflection mechanism and the jaw part tool.

At the distal end of the shaft 107, a deflection mechanism 149 comprises inside hinge bodies 153 and outside sleeves 151. On the distal side, the deflection mechanism 147 is connected to an end effector fork 147, which movably holds the end effector limbs 145 of the upper jaw part 141 and lower jaw part 143 of the jaw part tool 111 (see FIG. 2 and FIG. 4). The steering wires 117 guided on the inside around the hinge bodies 153 are held in a tube socket 155 and are steered inwardly in the proximal direction into the outer guide channels 135 and the inner guide channels 137 of the contoured guide 121. The outer guide channels 135 and the inner guide channels 137 are offset such that the tube socket is inserted and welded therein. A heat-shrink tubing 157 which also covers the connecting point between the contoured guide 121 and the tube socket (see FIG. 4) is arranged over the outer tube 127 to the outside.

The respective individual guidance of the ten steering wires 117 in an outer guide channel 135 or an inner guide channel 137 of the contoured guide 127 prevents a mix-up and twisting of the steering wires 117 during the assembly of the shaft 103. When the end portion 109 able to be deflected is deflected on account of a manipulation of the handle 113 by the user, a proximal drive (not shown here) impresses a movement on the tensioned steering wires 117 such that some of the circumferential steering wires 117 move through the associated guide channels 135, 137 in the direction toward the distal end 107 of the shaft 103 while the opposing steering wires 117 move through the associated guide channels 135, 137 in the direction toward the proximal end 105 of the shaft 103, whereby a corresponding deflecting movement of the end portion 109 able to be deflected of the distal-side deflection mechanism 149 is brought about. As a result, the contoured guide 121 with its star contour 123 in cross section enables an exactly guided movement of the steering wires 117 by way of the outer guide channels 135 and inner guide channels 137 adjoining the contour and hence a delicate deflecting of the end portion 109 able to be deflected, with the jaw part tool 111 connected thereto.

Figure 6:
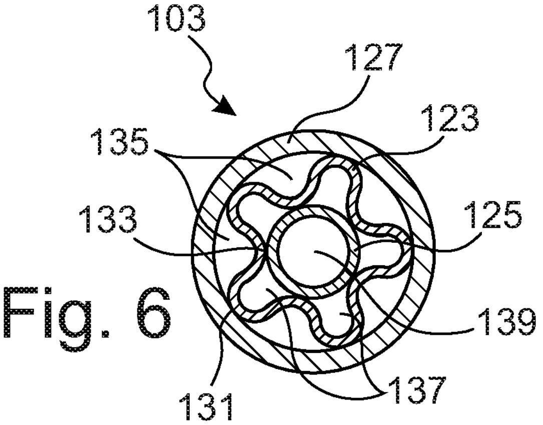

In the embodiment of the star contour 123 shown in FIG. 6, the bent star contour 123 has relatively large radii, wherein the outer contact points 131 of the star contour 123 at the inner side of the outer tube 127 have a greater dimension in the radial direction than the inner contact points 133 at the outer side of the inner tube 125. Accordingly, the five inner guide channels 137 and the five outer guide channels 135 each have the same radially symmetric cross-sectional shape.

Figure 5:
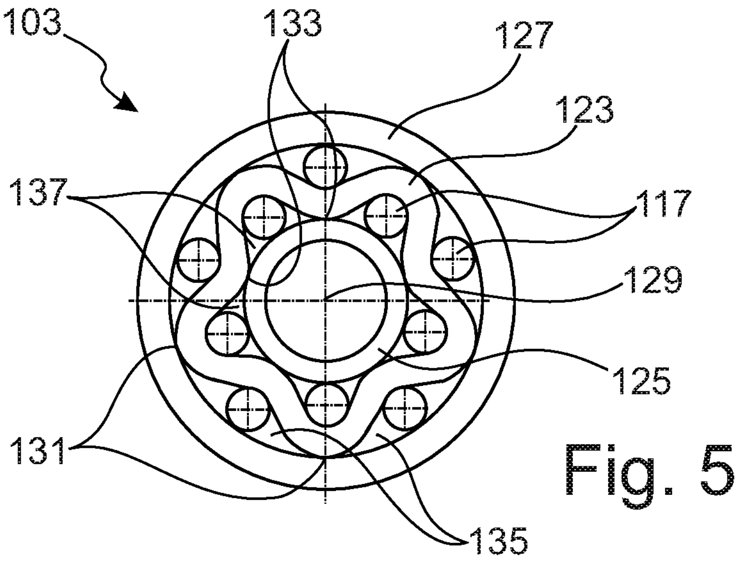
FIG. 5 shows a schematic sectional illustration through the cross section of the shaft with an alternative of a star contour of the contoured guide, FIGS. 6 to 10 each show a schematic sectional illustration of an alternative of the star contour and shaft in cross section.

In an alternative shown in FIG. 5, the star contour 123 has a more conically tapering embodiment at the outer contact points 131, whereby each of the five steering wires 117 in one of the five inner guide channels 137 is guided more tightly. As a result of the star contour 123 of this embodiment having a greater wall thickness, similar to the wall thickness of the outer tube 127, each of the five steering wires 117 guided in one of the five outer guide channels 135 is also guided more tightly. As a result of the greater wall thickness of the star contour 123, the shaft 103 is reinforced more in its interior.

Figure 7:
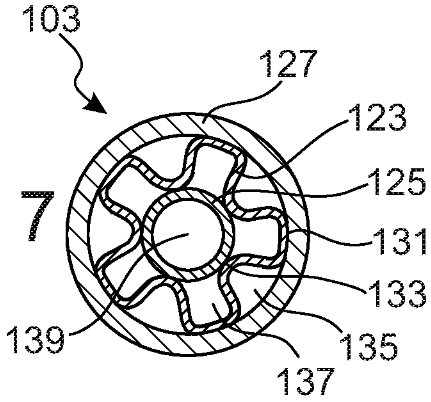

In a further alternative shown in FIG. 7, the radii at the start and end of each outer contact point 131 are bent around more strongly in comparison with the embodiment shown in FIG. 6, whereby it is possible, especially in the inner guide channels 137, to guide steering wires or steering cables with a slightly greater diameter.

Figure 8:
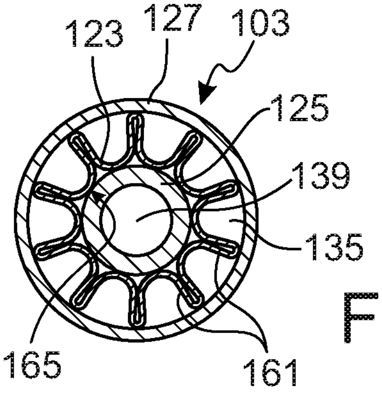

In a further alternative shown in FIG. 8, the outer tube 127 has a lesser wall thickness and the inner tube 125 has a greater wall thickness. The central channel 139 for guiding the pull/push rod 119 is arranged in the interior of the inner tube 125. In this embodiment there are ten outer guide channels 135, which are each separated by outwardly protruding ribs 161 formed by a respective bending of the star contour 123 in hard, tight radii through approximately 180° at the respective outer contact point 131 and hence two adjacent side walls of the star contour 123 are formed on the inside. The star contour 123 has a very thin wall thickness as a result of these hard, tight radii. The steering wires can already be placed directly into the outwardly open, ten outer guide channels 135 from the outside during the production of the shaft 103, before the outer tube 127 is pushed onto the contoured guide 121. Hence, this embodiment can dispense with the complex threading of the steering wires 117 through the guide channels. This is particularly advantageous if the steering wires 117 are already fastened on the distal and/or proximal side or have ends that are too thick to be threaded.

Hence, the star contour 123 in each case rests at the outer side of the inner tube 125 with a significantly larger dimension in the radial direction at the inner contact points 133 in comparison with the outer contact points 131. This forms a largely closed inner surface 165 of the star contour 123, which rests against the outer surface of the inner tube 125. The largely closed inner surface 165 around the inner tube 125 brings about increased strength and reinforcement in this region in a targeted manner.

Figure 10:
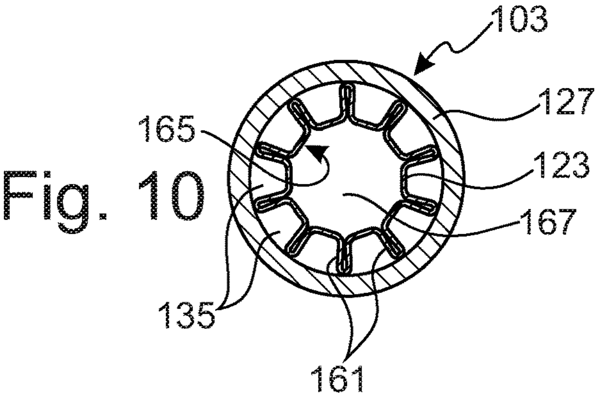

In a further alternative of the shaft 103 and star contour 123 shown in FIG. 10, a largely closed inner surface 165 of the star contour 123 is formed throughout to an even greater extent, with the result that it is possible to dispense with an inner tube 125 in this case since the largely closed inner surface 165 of the star contour 123 provides sufficient stiffness for the shaft 103. A pull/push rod 119 can be guided directly in a cavity 167 that is surrounded by the largely closed inner surface 165 of the star contour 123.

Figure 9:
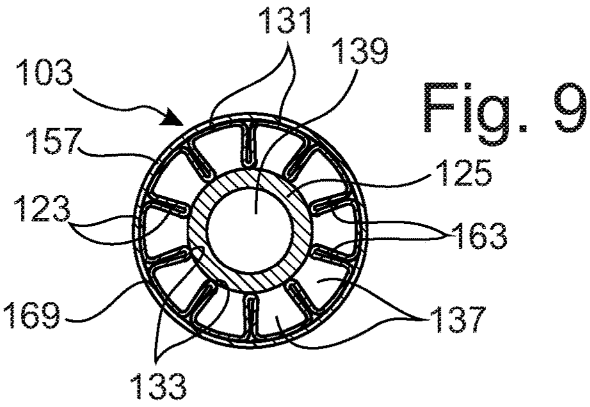

In a further alternative to the shaft 103, shown in cross section in FIG. 8, having the outwardly protruding ribs 161, inwardly protruding ribs 163 are formed on the outer surface of the inner tube 135 in a further alternative, wherein the star contour 123 accordingly has a thinner wall thickness (FIG. 9). Hence the inner contact points 133 have a very much smaller dimension than the outer contact points 131 and ten inner guide channels 137 are present. Accordingly, the outer contact points 133 of the star contour 123 form a largely closed outer surface 169 and a corresponding reinforcement. Therefore, an outer tube can be dispensed with in this embodiment and a heat-shrink tubing 157 can be applied directly to the largely closed outer surface 169 of the star contour 123.

Figure 11:
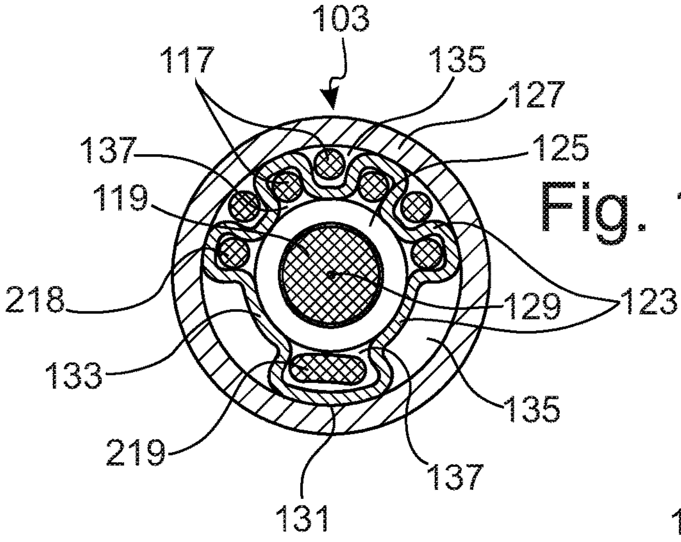
FIG. 11 shows a schematic sectional illustration through the cross section of a further alternative of the shaft with asymmetrically arranged guide channels.

In a further alternative of the shaft 103, shown in cross section in FIG. 11, the inner tube 127 is arranged concentrically with respect to the center 129 of the shaft 103. The pull/push rod 119 is guided in the central channel of the inner tube 125. In this embodiment, the star contour 123 is arranged asymmetrically but concentrically with respect to the center 129. As a result, a further manipulation element 219 with a wider cross section can additionally be guided separately in an inner guide channel 137. A cable 218 and six steering wires 117 are guided oppositely and in each case separately through in each case alternating inner guide channels 137 and outer guide channels 135.

Figure 12:
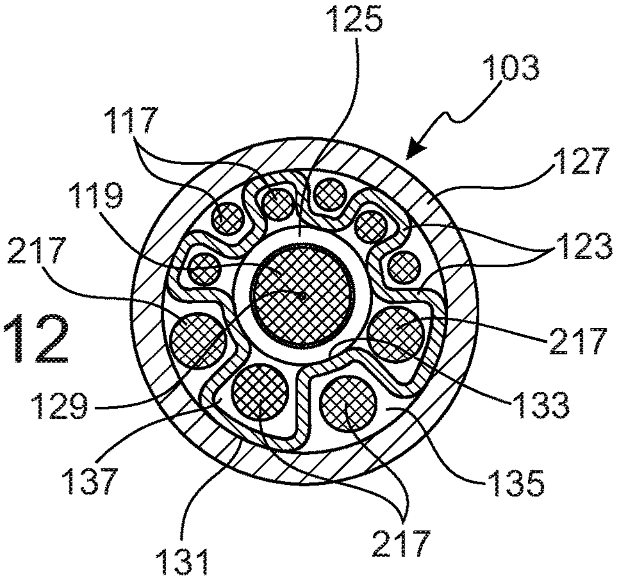
FIG. 12 shows a schematic sectional illustration of a further alternative of the shaft with an irregular arrangement of guide channels and an off-center arrangement of an inner tube.

In a further alternative, shown in FIG. 12, the star contour 123 is arranged off-center to the inner tube 125 arranged around its center 129 and the pull/push rod 119 guided on the inside in the central channel. The off-center arrangement of the star contour 123 makes space for forming, in alternation, a total of four outer guide channels 135 and inner guide channels 137 for accommodating thicker wires 217 in each case and an adjacent embodiment of the star contour 123 with tighter bends makes space for accommodating six further steering wires 117.

Figure 13:
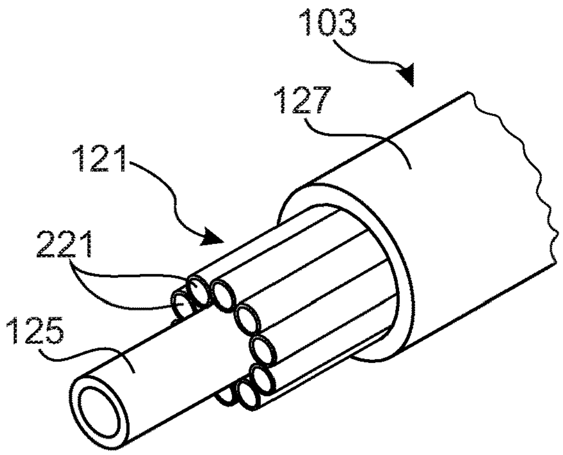
FIG. 13 shows a schematic, three-dimensional illustration of an alternative of the shaft with a contoured guide comprising standard guide tubes.

In a further alternative shown in FIG. 13, the contoured guide 121 is formed by ten, radially circumferentially adjacently arranged standard guide tubes 221 in place of a drawn specific contoured guide in the form of a star contour 123. In this case, the contoured guide 121 is arranged flush with outer and inner contact points between an outer tube 127 and an inner tube 125. The use of standard tubes means that the contoured guide 121 is significantly restricted in respect of the shaping of its own shape and the guide channel formed in the interior of the respective standard guide tube 221 and possible guide channels formed on the outside to the outer tube 123 and on the inside to the inner tube 125. However, the simple production from standard parts is advantageous in this embodiment.

Figure 14:
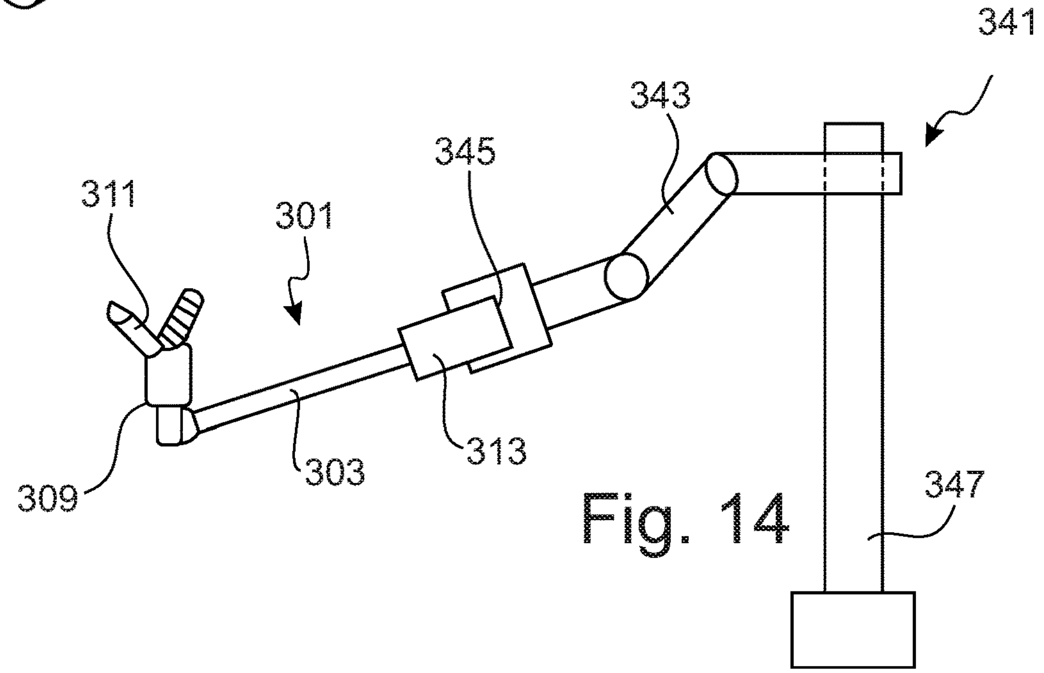
FIG. 14 shows a schematic illustration of a surgical robot having an endoscopic instrument fastened to a robotic arm.
Figure 15:
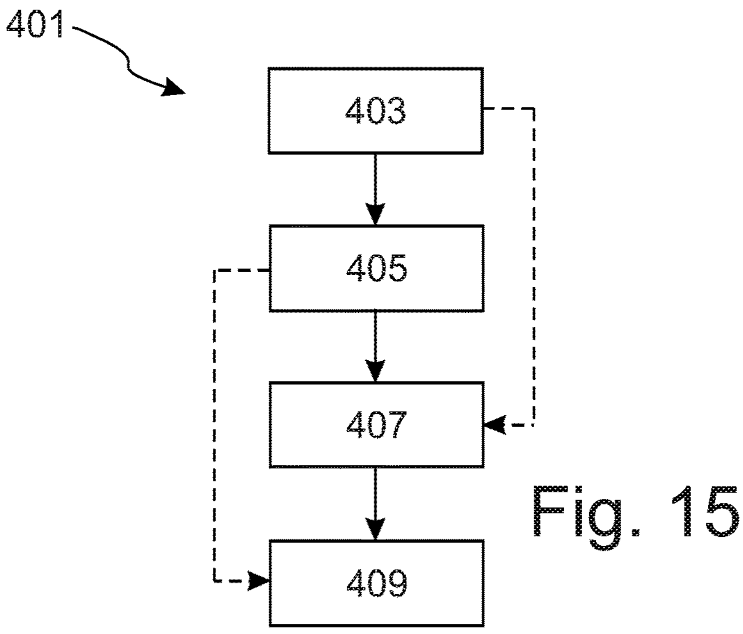
FIG. 15 shows an illustration of the steps of a method for producing a shaft.

In an alternative of the medical instrument 101, an endoscopic instrument 301 is formed as an end effector of a surgical robot 341. The surgical robot 341 has a base 374 with four robotic arms, with FIG. 14 only showing the one robotic arm 343 which holds the endoscopic instrument 301. In a manner analogous to FIG. 2, a shaft 303 of the endoscopic instrument 301 is formed with the contoured guide 121. At its distal end, the endoscopic instrument 301 comprises a tip 309 able to be deflected with a jaw tool 311 at the end (in FIG. 14, the jaw tool 311 is depicted in enlarged fashion and not true to scale). At the proximal end of the shaft 303, the endoscopic instrument 301 comprises a holding unit 313 which is held at the end of the robotic arm 334 of the surgical robot 341. An interface 345 for coupling purposes is arranged between the holding unit 313 of the endoscopic instrument 301 and the end of the robotic arm 343, a likewise interior proximal drive of the endoscopic instrument 301 being actuated at said interface via an interior actuator (not shown in FIG. 14) of the surgical robot 341. This impresses a movement on the distal-side hinge mechanism via the steering wires 117 and said movement is converted into a corresponding deflecting movement of the tip 309 able to be deflected.

On account of the embodiment of the contoured guide 121 in the shaft 303, a required flexural rigidity of the contoured guide 121 and shaft 303 is provided, this enabling the accurate positioning of the endoscopic instrument 301 by means of the robotic arm 343 of the surgical robot 341.

Figure 3:
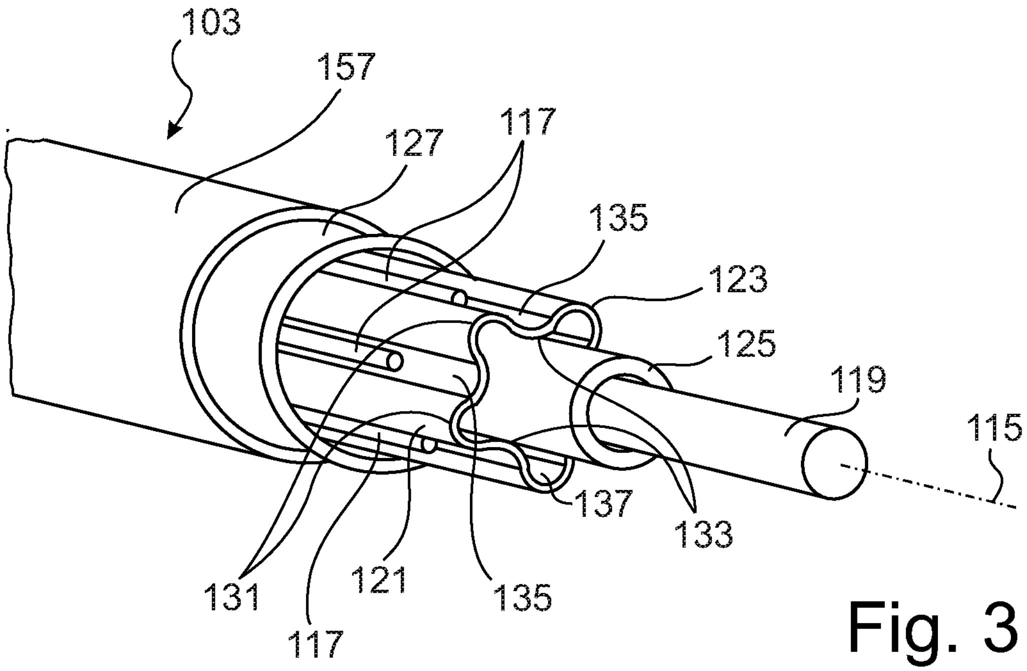
FIG. 3 shows a schematic three-dimensional illustration of a detail of the shaft with the contoured guide.

In a method 401 for producing the shaft 103 shown in FIGS. 3 and 6 the following work steps are carried out:

Initially, the contoured guide tube 121 with the star contour 123 in cross section is fabricated 403. For example, the contoured guide 121 is drawn if the material is steel. If the shaft 103 has an inner tube 125, the contoured guide tube 121 is subsequently joined 405 to the inner tube 125. If the shaft 103 has no inner tube 125, then the outer tube 127 is instead joined 407 directly to the contoured guide 121. Subsequently, the steering wires 117 are inserted into and/or threaded through the inner guide channels 137 and/or outer guide channels 135 adjacent to the contoured guide 121.

Optionally, if the shaft 103 does not have an outer tube 127, the steering wires 117 are inserted or threaded through 409 directly following the fabrication 403 of the contoured guide and the joining 405 of the contoured guide 121 to the inner tube 125.

Consequently, a shaft 103 is provided, the latter enabling an increased shaft stiffness and a simplified assembly of the steering wires 117 on account of the contoured guide 121 with the star contour 123 in cross section.

The drawings, the description, and the claims contain numerous features in combination. A person skilled in the art will advantageously also consider the features on an individual basis and combine them to form further advantageous combinations. The disclosure relates to a shaft for a medical instrument, the elongate shaft extending in a longitudinal direction from a proximal end to a distal end and having at its distal end an end portion, the end portion being able to be deflected relative to a longitudinal center axis of the shaft by means of a distal-side hinge mechanism and a tool being arrangeable at the end portion able to be deflected, and a plurality of steering elements for connecting a proximal-side drive to the distal-side hinge mechanism being guided through the interior of the shaft in the longitudinal direction, the shaft comprising an outer tube or an inner tube aligned in the longitudinal direction around a longitudinal center axis and the shaft comprising, between the outer tube and the longitudinal center axis or outside around the inner tube, an elongate contoured guide for guiding the steering elements, the contoured guide in the cross section across the longitudinal direction having a contour shape and the contour shape having at least a first contact point with the outer tube or inner tube, with the result that, between the outer tube and the contoured guide or between the contoured guide and the inner tube, one or more guide channels are formed in the longitudinal direction for guiding one or more steering elements. Moreover, the disclosure relates to a medical instrument, a robot, and a method for producing a shaft.

The invention claimed is:

1. A shaft for a medical instrument, the elongate shaft extending in a longitudinal direction from a proximal end to a distal end and having at its distal end an end portion, the end portion being able to be deflected relative to a longitudinal center axis of the shaft by means of a distal-side hinge mechanism and a tool being arrangeable at the end portion able to be deflected, and a plurality of steering elements for connecting a proximal-side drive to the distal-side hinge mechanism being guided through the interior of the shaft in the longitudinal direction, the shaft comprising:

an inner tube aligned in the longitudinal direction around a longitudinal center axis;

an outer tube concentric to the inner tube; and an elongate contoured guide for guiding the steering elements, the elongated contoured guide disposed between the outer tube and the inner tube, the elongated contoured guide folded about a contact point onto itself to form a plurality of ribs and a plurality of curved portions disposed between a pair of the plurality of ribs, the plurality of ribs extending between the inner tube and the outer tube to define a plurality of guide channels extending in the longitudinal direction for guiding one or more steering elements.

2. The shaft set forth claim 1, wherein the plurality of curved portions are seated against an outer surface of the inner tube and the contact point is pressed against an inner surface of the outer tube.

3. The shaft as set forth in claim 1, wherein the plurality of curved portions are seated against an inner surface of the outer tube and the contact point is pressed against an outer surface of the inner tube.

4. The shaft as set forth in claim 1, wherein the elongated contoured guide is radially symmetrical, polysymmetrical, and/or asymmetrical in cross section.

5. The shaft as set forth in claim 1, wherein each of the plurality of ribs includes a first wall and a second wall folded onto each other about the contact point and the first wall and the second wall are closed onto each other.

6. The shaft as set forth in claim 1, wherein an insulation tubing is arranged around the elongated contoured guide.

7. The shaft as set forth in claim 1, wherein the outer tube, the elongated contoured guide, and/or the inner tube is or are arranged coaxially with or off-center in relation to the longitudinal center axis of the shaft.

8. The shaft as set forth in claim 1, wherein an elongate manipulation element for manipulating the tool is guided in the inner tube and/or in one of the plurality of guide channels.

9. The shaft as set forth in claim 1, wherein the outer tube, the inner tube, and/or the elongated contoured guide contain a metal, a metal alloy, plastic, and/or a fiber-reinforced material.

10. The shaft as set forth in claim 9, wherein the fiber-reinforced material is formed by a plurality of fibers and each of the plurality of fibers are aligned in radially circumferential fashion around a longitudinal center axis of the outer tube, inner tube, and/or elongated contoured guide.

11. A medical instrument having an elongate shaft and a handling unit connected to the elongated shaft as set forth in claim 1, with the handling unit rendering manipulatable a proximal drive of a distal-side hinge mechanism and/or an elongate manipulation element for manipulating a tool at an end portion able to be deflected at the distal end of the elongated shaft, wherein one or more steering elements are guided through one or more guide channels in the contoured guide.

12. A robot having at least one robotic arm for holding and/or positioning a medical instrument and/or having an actuator for controlling a distal-side hinge mechanism of the medical instrument, wherein the medical instrument is a medical instrument as set forth claim 11, with the result that the medical instrument is positionable by means of the at least one robotic arm and/or the distal-side hinge mechanism is manipulatable by the action of the actuator of the robot on the proximal drive of the medical instrument.

13. A shaft for a medical instrument, the elongate shaft extending in a longitudinal direction from a proximal end to a distal end and having at its distal end an end portion, the end portion being able to be deflected relative to a longitudinal center axis of the shaft by means of a distal-side hinge mechanism and a tool being arrangeable at the end portion able to be deflected, and a plurality of steering elements for connecting a proximal-side drive to the distal-side hinge mechanism being guided through the interior of the shaft in the longitudinal direction, the shaft comprising:

an inner tube aligned in the longitudinal direction around a longitudinal center axis;

an outer tube concentric to the inner tube; and an elongate contoured guide for guiding the steering elements between the inner tube and the outer tube, the elongated contoured guide disposed between the outer tube and the inner tube, the elongated contoured guide including plurality of first contact points spaced apart from each other and contacting a portion of an inner surface of the outer tube along a first arc length and a plurality of second contact points contacting a portion of an outer surface of the inner tube along a second arc length so as to form a plurality of first guide channels disposed between an outer surface of the elongate contoured guide and the inner surface of the outer tube and a plurality of second guide channels disposed between an inner surface of the elongate contoured guide and the outer surface of the inner tube; and a third contact point spaced apart from the first contact point and the second contact point, the third contact point contacting a portion of the inner surface of the outer tube along a third arc length greater than the first contact point and the second contact point so as to form a third guide channel having an area greater than an area of each of the plurality of first guide channels and second guide channels.

14. The shaft as set forth in claim 13, wherein the second arc length is equal to the first arc length.

15. The shaft as set forth in claim 13, wherein each of the plurality of first guide channels and the plurality of second guide channels are configured to accommodate one of a steering wire and a cable and the third guide channel is configured to accommodate a further manipulation element that is thicker than one of the steering wire and cable.

16. The shaft as set forth in claim 13, wherein the third guide channel is at least one third guide channel.

* * * * *